Sept. 23, 1958 E. S. BOERNER Plant Pat. 1,757
ROSE PLANT
Filed Feb. 24, 1958
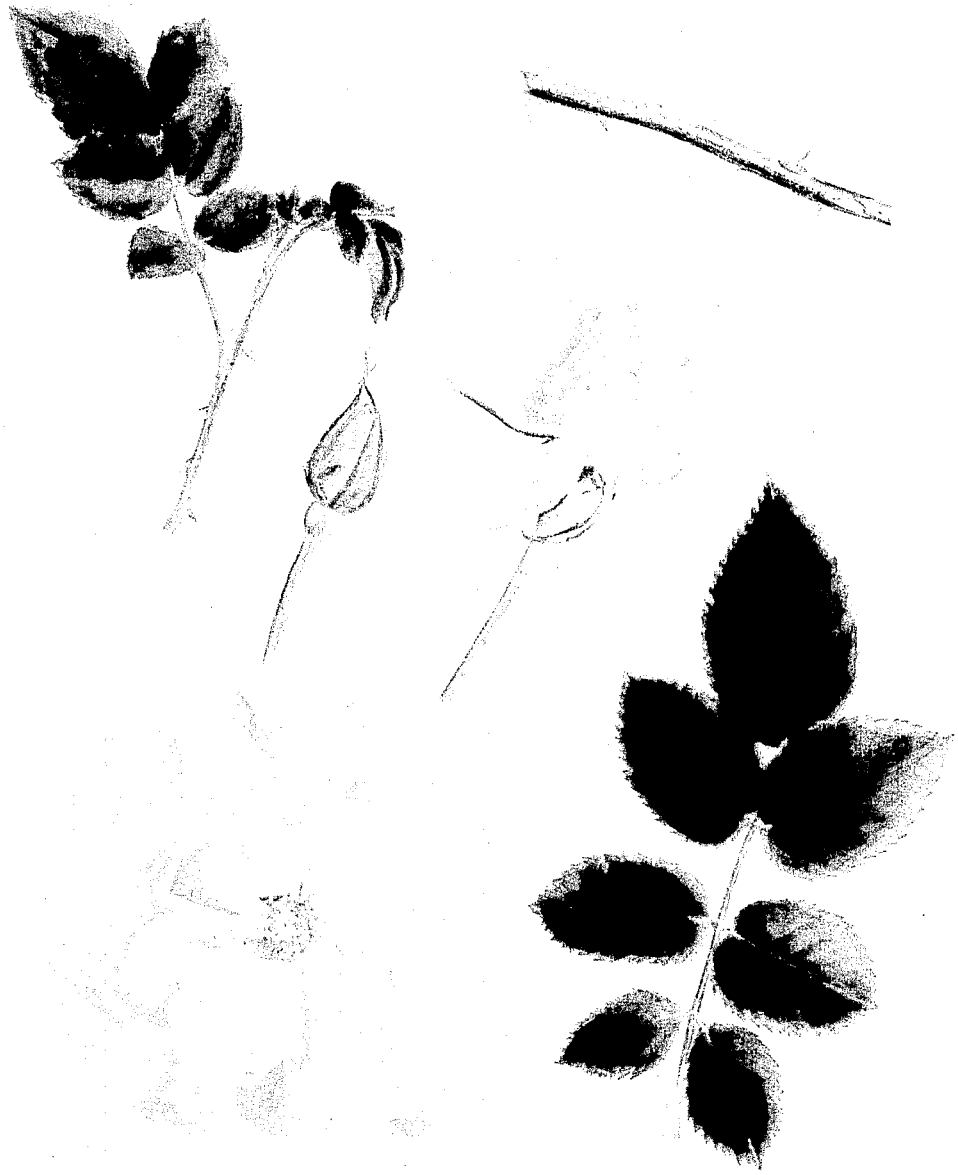
Inventor.
E. S. Boerner
By: Robb & Robb
Attorneys.

United States Patent Office

Plant Pat. 1,757
Patented Sept. 23, 1958

1,757

ROSE PLANT

Eugene S. Boerner, Newark, N. Y., assignor to Jackson & Perkins Company, Newark, N. Y., a corporation of New York Application February 24, 1958, Serial No. 717,282

1 Claim. (Cl. 47—61)

The present invention relates to a new and distinct variety of rose plant of the large-flowered polyantha class, which was originated by me by crossing the variety "Ma Perkins" (Plant Patent No. 1,143) with an unnamed and unpatented Floribunda seedling.

The primary objective of this breeding was to produce a new rose variety which bears flowers of a more intense color than those of the parent variety "Ma Perkins," while still retaining the other characteristics of this parent. This objective was fully achieved, along with other desirable improvements, as evidenced by the following characteristics which are outstanding in the new variety and represent a unique combination which is distinguished from the parents aforesaid, as well as from all other varieties of which I am aware:

(1) Vigorous and compact habits of growth;

(2) Abundant flowers, which, together with the compact form of the plant, makes the new variety ideal for pot forcing;

(3) Long-lasting quality of the flowers; and (4) A distinctive general color tonality of the flowers, corresponding to Geranium Pink, lightly overcast with Eosine Pink.

Asexual reproduction of my new variety, by budding, as performed at Newark, New York and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminalogy in accordance with Ridgway's Color Standards and Nomenclature:

Parentage: Seedling.

*Seed parent.*—"Ma Perkins."

*Pollen parent.*—An unnamed Floribunda seedling.

Classification:

*Botanic.*—Large-flowered polyantha.

*Commercial.*—Floribunda.

*Flower*

(Observations made from specimens grown in a greenhouse at Newark, New York, in the early morning and in the early part of October).

Blooming Habit: Recurrent—Continuous.

Bud:

*Size.*—Medium.

*Form.*—Ovoid; is not affected by wet or hot weather.

*Color.*—When sepals first divide—Scarlet, Plate 1. When petals begin to unfurl—Scarlet, Plate 1, lightly overcast with Peach Red, Plate 1. When half-blown: inside of petals—Rose Doree, Plate 1, lightly overcast with Peach Red, Plate 1; reverse of petals—Begonia Rose, Plate 1, with lower half of petal lightly overcast with Peach Red, Plate 1.

*Sepals.*—Slightly branched; curl back when petals begin to unfurl. Color: inside—Pale Fluorite Green, Plate 32. outside—Light Cress Green, Plate 31.

*Calyx.*—Color—Biscay Green, Plate 17. Shape—pear. Size—small. Aspect—smooth. Odor when rubbed—none.

*Peduncle.* — Length — medium. Aspect — smooth. Strength—erect; slender. Color—Biscay Green, Plate 17.

*Opening.*—Opens up well; is not affected by adverse weather conditions.

Bloom:

*Size.*—Medium. Average size when fully expanded—4 inches.

*Borne.*—Both singly and several together.

*Stems.*—Medium length; normal strength.

*Form (when first open).*—Cupped. Permanence—retains its form to the end, but outer petals curl back.

*Petalage.*—Double (full but open center). Number of petals under normal conditions—From 35 to 40.

*Color.*—Center of flower—Geranium Pink, Plate 1, with lower half of petals lightly overcast with Grenadine Pink, Plate 2. Outer petals—Eosine Pink, Plate 1, lightly overcast with Thulite Pink, Plate 26 on the outer edge of the petals. Base of petals (aiglet)—Lemon Yellow, Plate 4. Inside of petals—Geranium Pink, Plate 1, lightly overcast with Eosine Pink, Plate 1. Reverse of petals—La France Pink, Plate 1, lightly overcast with Grenadine Pink, Plate 2. General tonality from a distance—Geranium Pink, Plate 1, lightly overcast with Eosine Pink, Plate 1.

*Discoloration.*—General tonality at end of first day—Geranium Pink, Plate 1. Second day—Geranium Pink, Plate 1, lightly overcast with Eosine Pink, Plate 1. Third day—Eosine Pink, Plate 1, lightly overcast with Thulite Pink, Plate 26.

Petals:

*Texture.*—Leathery; is not affected by wet or hot weather.

*Appearance.*—Inside—shiny. Outside—satiny.

*Form.*—Oval.

*Arrangement.* — Imbricated (regularly arranged shingle-like).

*Petaloids in center.*—Few; small.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Medium size; many; regularly arranged around styles. Color—Empire Yellow, Plate 4.

Stamens, filaments (threads): Medium length. Color—Deep Chrome, Plate 3.

Pollen: Color—Pale Orange Yellow, Plate 3.

Styles: Bunched; uneven length; medium length; thin.

Stigmas: Color—Picric Yellow, Plate 4.

Ovaries: All enclosed in calyx.

Hips: None.

Seeds: None.

*Plant*

Form: Bush.

Growth: Vigorous; compact.

Foliage: Compound of 5 to 7 leaflets.

*Size.*—Medium.

*Quantity.*—Normal.

*Color.*—New foliage: upper side—Spinach Green, Plate 5, with outer edges lightly overcast with Bordeaux, Plate 12; under side—Mignonette Green, Plate 31, lightly overcast with Bordeaux, Plate 12. Old foliage: upper side—Dark Cress Green, Plate 31; under side—Light Cress Green, Plate 31.

*Shape.*—Oval pointed.

*Texture.* — Upper side — leathery. Under side—smooth.

*Ribs and veins.*—Ordinary.

*Edge.*—Serrated (saw-toothed).

*Serration.*—Both double and single; small.

*Leaf stem.*—Color—Purplish Vinaceous, Plate 39. Under side—smooth.

*Stipules.*—Medium length; bearded.

Wood:

*New wood.*—Color—Rainette Green, Plate 31, lightly overcast with Carmine, Plate 1. Bark—smooth.

*Old wood.*—Color—Light Cress Green, Plate 31. Bark—smooth.

Thorns:

*Thorns.*—Quantity: on main stalks from base—few; on laterals from stalk—few. Form—narrow base; short; hooked downward. Color (when young)—Begonia Rose, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the unique combination of vigorous and compact habits of growth, abundance of flowers, with attendant suitability for pot-forcing, long-lasting quality of the flowers, and a distinctive Geranium Pinw lightly overcast with Eosine Pink general color tonality of the flowers.

No references cited.

UNITED STATES PATENT OFFICE

CERTIFICATE OF CORRECTION

Plant Patent No. 1,757 September 23, 1958

Eugene S. Boerner

It is hereby certified that error appears in the printed specification of the above numbered patent requiring correction and that the said Letters Patent should read as corrected below.

Column 4, line 17, for "Geranium Pinw" read -- Geranium Pink --.

Signed and sealed this 2nd day of December 1958.

(SEAL)
Attest:

KARL H. AXLINE
Attesting Officer

ROBERT C. WATSON
Commissioner of Patents